(12) United States Patent
Shiller et al.

(10) Patent No.: US 11,963,690 B2
(45) Date of Patent: *Apr. 23, 2024

(54) DEVICES AND METHODS FOR TREATING EPISTAXIS

(71) Applicant: JMK50, LLC, Colorado Springs, CO (US)

(72) Inventors: Joseph Shiller, Colorado Springs, CO (US); Melissa Howard, Colorado Springs, CO (US)

(73) Assignee: JMK50, LLC, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/225,759

(22) Filed: Jul. 25, 2023

(65) Prior Publication Data

US 2023/0363779 A1 Nov. 16, 2023

Related U.S. Application Data

(63) Continuation of application No. 17/972,779, filed on Oct. 25, 2022, now Pat. No. 11,707,291.

(60) Provisional application No. 63/271,389, filed on Oct. 25, 2021.

(51) Int. Cl.
*A61B 17/24* (2006.01)
*A61B 17/12* (2006.01)

(52) U.S. Cl.
CPC .................. *A61B 17/24* (2013.01)

(58) Field of Classification Search
CPC ............. A61B 17/24; A61B 17/244; A61B 2017/12004; A61B 2017/246; A61B 2017/242; A61F 5/08; A61F 5/56; A61F 13/2005; A61F 13/15; A61F 13/20; A61F 13/2051; A61F 13/2022; A61F 2/186; A61F 2/18; A62B 9/06
See application file for complete search history.

(56) References Cited

U.S. PATENT DOCUMENTS

| | | | |
|---|---|---|---|
| 9,855,054 | B1 | 1/2018 | Stcyr |
| 10,206,684 | B2 | 2/2019 | Ibarra |
| 10,426,502 | B2 | 10/2019 | Moloney |
| 10,806,476 | B2 | 10/2020 | Randall |
| 10,925,608 | B2 | 2/2021 | Ibarra |

(Continued)

OTHER PUBLICATIONS

International Search Report and Written Opinion dated Feb. 2, 2023 for Application No. PCT/US22/78648.

*Primary Examiner* — Majid Jamialahmadi
(74) *Attorney, Agent, or Firm* — Patterson + Sheridan, LLP

(57) ABSTRACT

The present disclosure relates to devices and methods for treating epistaxis. In some embodiments, a device for occluding epistaxis includes a first curvilinear wall, a second curvilinear wall, and a third curvilinear wall each disposed at a top portion of the device. The device has an x-axis, y-axis, and z-axis, and the top portion is relative to the y-axis. The device includes a fourth wall and a fifth wall each disposed at a bottom portion relative to the y-axis of the device. The fourth wall and the fifth wall independently are substantially straight or curvilinear. The device includes a first end including a front first end portion and a back first end portion. The first end is curvilinear corresponding to the first curvilinear wall, and the first end is disposed at an angle relative to the x-axis.

29 Claims, 8 Drawing Sheets

(56) References Cited

U.S. PATENT DOCUMENTS

| | | |
|---|---|---|
| 2004/0194788 A1 | 10/2004 | Sweet |
| 2016/0030253 A1 | 2/2016 | Husain |
| 2017/0020742 A1 | 1/2017 | Rix |
| 2019/0133589 A1 | 5/2019 | Ibarra |
| 2020/0138180 A1 | 5/2020 | Arbeitman et al. |
| 2022/0160384 A1* | 5/2022 | Ibarra ................. A61B 17/132 |

* cited by examiner

DEVICES AND METHODS FOR TREATING EPISTAXIS

CROSS-REFERENCE TO RELATED APPLICATIONS

This application is a continuation of U.S. Non-Provisional patent application Ser. No. 17/972,779, filed Oct. 25, 2022, which claims the benefit of U.S. Provisional Patent Application Ser. No. 63/271,389, filed Oct. 25, 2021, which are incorporated by reference herein in their entirety.

FIELD

The present disclosure relates to devices and methods for treating epistaxis.

BACKGROUND

Epistaxis (also referred to as a nosebleed) tends to occur frequently with some individuals much more than with others. Epistaxis may occur after stress or exercise or due to dry air conditions or other irritations of the nasal interior tissues. In particular, 90% of epistaxis arises from the small area along the caudal septum. Blood supply to this area is from the Kiesselbach plexus which is composed of second-order branches of the internal and external carotid artery systems. Hemorrhage in this area is commonly referred to as anterior epistaxis.

A typical method for treating epistaxis in a patient includes positioning the patient upright, leaning forward slightly and firmly pinching the outside of the nose with the thumb and index fingers against the face at a location just below the bone. Other methods include applying cold packs, cauterization, nasal packing, or even surgery. However, pinching the nose, cauterization, nasal packing, and surgery usually cause discomfort/pain to the patient, may be ineffective, and/or involve a substantial amount of time for bleeding to cease.

For example, a nasal tampon is the most common device used by providers to mitigate anterior epistaxis. The nasal tampon is inserted into the nostril by the applicator and leaves an absorbent wad/packing in the nostril. Although nasal tampons are fast effective methods in the mitigation of anterior epistaxis, nasal tampons also provide painful insertion and removal from the nostril, potential induced trauma to the nostril, and nasal occlusion during use which inhibits a user's airway. Upon removal of a nasal tampon, the blood clot formed in the nostril can break and allow bleeding to continue due to adherence of the nasal tampon to the blood clot. In addition, there is no way to assess that a hemorrhage has stopped without removal of the tampon from the nostril and bleeding might still be occurring upon removal of the nasal tampon. Lastly, extensive training is needed for effective insertion and removal of the nasal tampon.

Another device used to treat epistaxis is a balloon-containing device that is inserted into the nasal cavity and inflated. This balloon-containing device has the same disadvantages of the nasal tampons, yet a balloon-containing device could exacerbate the base of a skull fracture potentially displacing the fracture into the cranial vault.

Another device for treating epistaxis includes placing a "pressure insert" between a person's gum and upper lip near the frenulum. However, such pressure inserts have proven ineffective and/or visually unappealing. For example, a pressure insert present only between the user's gum and upper lip tends to not maintain its position near the frenulum for a sufficient period of time to terminate anterior epistaxis (or the pressure insert will slide out of a user's mouth entirely). To assist this issue, pressure inserts have been proposed that have a bite tab, a designated push surface on the bottom of the pressure insert, or a stem attached to the bottom of the insert portion. However, pressure inserts having a bite tab, push surface, or stem require action by the user to hold the insert in place and/or adjust the position of the pressure insert, which highlights the tendency of current pressure inserts to not have an ability to maintain their position between the upper lip and the gingiva of a user and stop the anterior epistaxis, inevitably delaying the stoppage of the anterior epistaxis. In addition, pressure inserts having a bite tab, push surface, or stem are bulky in size such that the user and an outside observer (i.e., someone besides the user) can clearly see that a large object is present in the user's buccal cavity.

There is a need for improved devices for stopping epistaxis.

BRIEF SUMMARY

The present disclosure relates to devices and methods for treating epistaxis.

In some embodiments, a device for occluding epistaxis includes one or more apertures.

In some embodiments, a device for occluding epistaxis includes a first curvilinear wall, a second curvilinear wall, and a third curvilinear wall each disposed at a top portion of the device. The device has an x-axis, y-axis, and z-axis, and the top portion is relative to the y-axis. The device includes a fourth wall and a fifth wall each disposed at a bottom portion relative to the y-axis of the device. The fourth wall and the fifth wall independently are substantially straight or curvilinear. The device includes a first end including a front first end portion and a back first end portion. The first end is curvilinear corresponding to the first curvilinear wall, and the first end is disposed at an angle relative to the x-axis. The device includes a second end including a front second end portion and a back second end portion. The second end is curvilinear and continuous with the third curvilinear wall, and the second end disposed at an angle relative to the x-axis. The device includes a middle portion including a front middle portion and a back middle portion. The middle portion is curvilinear and continuous with the second curvilinear wall. The device includes one or more protrusions having a substantially vertical orientation relative to the y-axis. The device includes one or more apertures disposed through the device.

In some embodiments, a device for occluding epistaxis includes a first curvilinear wall, a second curvilinear wall, and a third curvilinear wall each disposed at a top portion of the device. The device has an x-axis, y-axis, and z-axis. The top portion is relative to the y-axis. The device includes a fourth wall and a fifth wall each disposed at a bottom portion of the device. The fourth wall and the fifth wall independently are substantially straight or curvilinear. The device includes a first end including a front first end portion and a back first end portion. The first end is curvilinear corresponding to the first curvilinear wall. The first end is disposed at an angle relative to the x-axis. The device includes a second end including a front second end portion and a back second end portion. The second end is curvilinear and continuous with the third curvilinear wall. The second end is disposed at an angle relative to the x-axis. The device includes a middle portion including a front middle portion and a back middle portion. The middle portion is curvilinear and continuous with the second curvilinear wall. The device includes one or more apertures disposed through the device.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this present disclosure and are therefore not to be considered limiting of its scope, for the present disclosure may admit to other equally effective aspects.

Figure 1A:
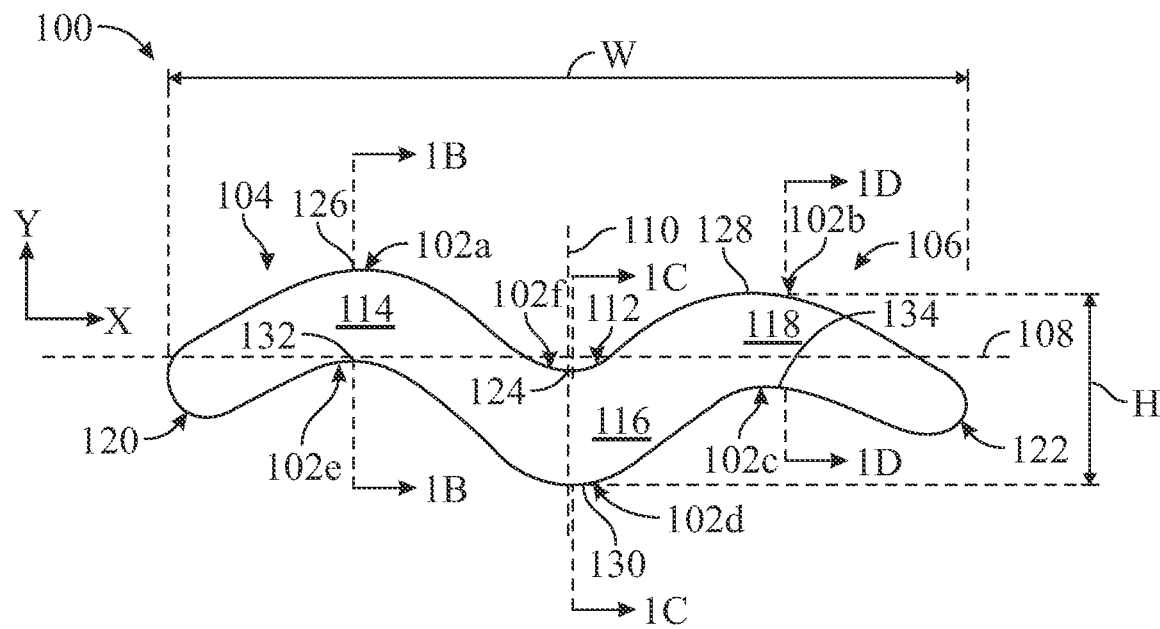
FIG. 1A is a front view illustrating a device for ceasing epistaxis, according to an embodiment.

To facilitate understanding, identical reference numerals have been used, where possible, to designate identical elements that are common to the figures. The figures are not drawn to scale and may be simplified for clarity. It is contemplated that elements and features of one aspect may be beneficially incorporated in other aspects without further recitation.

DETAILED DESCRIPTION

The present disclosure relates to devices and methods for treating epistaxis. Devices and methods of the present disclosure provide amelioration of continual positional adjustment by the user and are inconspicuous to outside observers during use by the user. The inventors have discovered that a device that is a material having curvilinear sidewalls, where the curvilinear sidewalls have a plurality of protrusions and/or apertures, provides non-invasive, painless devices for treating (e.g., ceasing) epistaxis. Devices and methods of the present disclosure do not require continual positional adjustment by the user, and the devices are substantially or entirely inconspicuous to outside observers during use by the user. Devices of the present disclosure are a simply inserted oral device which creates occlusion of the structures associated with anterior epistaxis, occluding the flow of blood to the location of the hemorrhage responsible for the epistaxis. In addition, protrusions and/or apertures of devices of the present disclosure provide (1) the device to stay in place while occluding flow of blood to a hemorrhage and (2) substantial or complete reduction in risk of a user inadvertently swallowing the device. In the event a device might be swallowed, devices of the present disclosure may include one or more apertures such that air can flow through the one or more apertures.

In addition, devices of the present disclosure can occlude a hemorrhage to stop anterior epistaxis without nasal packing, unlike a nasal tampon, leaving the nostril free from obstruction. Insertion and removal of devices of the present disclosure is painless, providing less fear for a user. In addition, risk of opening a clot upon removal of the device is substantially less (e.g., eliminated), as compared to nasal tampons and balloon-like devices. In addition, devices of the present disclosure do not require substantial training on how to use the devices, as compared to nasal tampons and balloon-like devices. In addition, devices of the present disclosure are small (e.g., as compared to devices having a stem or a bite tab) making the devices easy to transport without taking up substantial space (e.g., the devices can be transported in a user's pocket).

In some embodiments which can be combined with other embodiments, a device for occluding epistaxis includes one or more apertures.

In some embodiments, a device for occluding epistaxis includes a first curvilinear wall, a second curvilinear wall, and a third curvilinear wall each disposed at a top portion of the device. The device has an x-axis, y-axis, and z-axis, and the top portion is relative to the y-axis. The device includes a fourth wall and a fifth wall each disposed at a bottom portion relative to the y-axis of the device. The fourth wall and the fifth wall independently are substantially straight or curvilinear. The device includes a first end including a front first end portion and a back first end portion. The first end is curvilinear corresponding to the first curvilinear wall, and the first end is disposed at an angle relative to the x-axis. The device includes a second end including a front second end portion and a back second end portion. The second end is curvilinear and continuous with the third curvilinear wall, and the second end disposed at an angle relative to the x-axis. The device includes a middle portion including a front middle portion and a back middle portion. The middle portion is curvilinear and continuous with the second curvilinear wall. The device includes one or more protrusions having a substantially vertical orientation relative to the y-axis. The device includes one or more apertures disposed through the device.

In some embodiments, a device for occluding epistaxis includes a first curvilinear wall, a second curvilinear wall, and a third curvilinear wall each disposed at a top portion of the device. The device has an x-axis, y-axis, and z-axis. The top portion is relative to the y-axis. The device includes a fourth wall and a fifth wall each disposed at a bottom portion of the device. The fourth wall and the fifth wall independently are substantially straight or curvilinear. The device includes a first end including a front first end portion and a back first end portion. The first end is curvilinear corresponding to the first curvilinear wall. The first end is disposed at an angle relative to the x-axis. The device includes a second end including a front second end portion and a back second end portion. The second end is curvilinear and continuous with the third curvilinear wall. The second end is disposed at an angle relative to the x-axis. The device includes a middle portion including a front middle portion and a back middle portion. The middle portion is curvilinear and continuous with the second curvilinear wall. The device includes one or more apertures disposed through the device. Devices Devices of the present disclosure, when placed between the upper lip and the gingiva of a user, are configured to occlude blood to a hemorrhage by applying pressure to the user's superior labial artery, the Kiesselbach plexus, and/or the greater palatine artery. By applying gentle pressure to this area, the blood is occluded at the hemorrhage.

In some embodiments, a device is a material having curvilinear sidewalls. For example, the curvilinear sidewalls might not be horizontally extending, but instead the device has a first end and second end where the first end and/or second end are disposed at an angle relative to a horizontal axis. For example, the first end can extend from a first curvilinear portion in a direction that is not parallel with the horizontal axis and is not orthogonal to the vertical axis. The second end can extend from a second curvilinear portion in a direction that is not parallel with the horizontal axis and is not orthogonal to the vertical axis.

A device has a gap portion shaped to fit around (e.g., nest with) a user's frenulum such that the device does not interfere with the frenulum but nonetheless provides amelioration of epistaxis by occluding blood to a hemorrhage by applying pressure to the user's superior labial artery, the Kiesselbach plexus, and/or the greater palatine artery.

In some embodiments, the curvilinear sidewalls have a plurality of protrusions and/or one or more apertures such that air can flow through the one or more apertures.

FIG. 1A is a front view of a device 100. Device 100 is a serpentine-shaped material having curvilinear sidewalls 102a, 102b, 102c, 102d, 102e, and 102f. Curvilinear sidewalls 102a and 102b can apply pressure during use to the user's superior labial artery, the Kiesselbach plexus, and/or the greater palatine artery.

The curvilinear sidewalls 102a-102f are not horizontally extending, but instead the device 100 has a first end 104 and second end 106 where the first end 104 and the second end 106 are disposed at an angle relative to a horizontal axis 108.

For example, the first end 104 can extend from a first curvilinear portion (e.g., apex point 126 of sidewall 102a to valley point 124 and/or to end cap 120) in a direction that is not parallel with the horizontal axis 108 and is not orthogonal to the vertical axis 110. The second end 106 can extend from a second curvilinear portion (e.g., apex point 128 of sidewall 102b to valley point 124 and/or to end cap 122) in a direction that is not parallel with the horizontal axis 108 and is not orthogonal to the vertical axis 110.

Device 100 has a front first end portion 114, a front second end portion 118, and a front middle portion 116. The front first end portion 114 has a curvilinear shape corresponding to curvilinear sidewall 102a and curvilinear sidewall 102e. A rear first end portion (not shown) is disposed on a side opposite of front first end portion 114, and the rear first end portion has a curvilinear shape corresponding to curvilinear sidewall 102a and curvilinear sidewall 102e.

The front second end portion 118 has a curvilinear shape corresponding to curvilinear sidewall 102b and curvilinear sidewall 102c. A rear second end portion (not shown) is disposed on a side opposite of front second end portion 118, and the rear first end portion has a curvilinear shape corresponding to curvilinear sidewall 102b and curvilinear sidewall 102c.

The front middle portion 116 has a curvilinear shape corresponding to curvilinear sidewall 102d and curvilinear sidewall 102f. A rear middle portion (not shown) is disposed on a side opposite of front middle portion 116, and the rear middle portion has a curvilinear shape corresponding to curvilinear sidewall 102a and curvilinear sidewall 102e.

Device 100 has a gap portion 112 shaped to fit around (e.g., nest with) a user's frenulum such that the device does not interfere with the frenulum and the device provides occlusion of a hemorrhage promoting epistaxis during use. Gap portion 112 has a valley point 124 (of sidewall 102f) provided by the descent of sidewall 102a from apex point 126 toward horizontal axis 108 and provided by the descent of sidewall 102b from apex point 128 toward horizontal axis 108.

Sidewall 102e has a valley point 132 disposed opposite the apex point 126 of sidewall 102a. Sidewall 102d has an apex point 130 disposed opposite valley point 124 of sidewall 102f. Sidewall 102c has a valley point 134 disposed opposite apex point 128 of sidewall 102b. In some embodiments, valley point 134 is aligned with valley point 132 and valley point 134 along horizontal axis 108.

Device 100 has a first end cap 120 and a second end cap 122. First end cap 120 and second end cap 122 are independently selected from dome-shaped (as shown in FIG. 1A), pointed (e.g., conical ending in a point), or tapered. However, other suitable shapes for the first end cap 120 and second end cap 122 are contemplated.

In some embodiments which can be combined with other embodiments, device 100 has a width (W) (e.g., linear distance from first end cap 120 to second end cap 122) of about 50 millimeters (mm) to about 70 mm, such as about 55 mm to about 65 mm, such as about 57 mm to about 60 mm, such as about 58 mm. In some embodiments which can be combined with other embodiments, device 100 has a height (H) (e.g., vertical distance from peak points 126 and 128 to peak point 130) of about 10 mm to about 18 mm, such as about 12 mm to about 16 mm, such as about 13 mm to about 15 mm, such as about 14 mm.

Alternatively, device 100 has a width (W) (e.g., linear distance from first end cap 120 to second end cap 122) of about 25 millimeters (mm) to about 50 mm, such as about 28 mm to about 40 mm, such as about 29 mm to about 31 mm, alternatively about 36 mm to about 38 mm. In some embodiments, device 100 has a height (H) (e.g., vertical distance from peak points 126 and 128 to peak point 130) of about 4 mm to about 15 mm, such as about 4 mm to about 7 mm, alternatively about 9 mm to about 11 mm, such as about 10 mm.

Figure 1B:
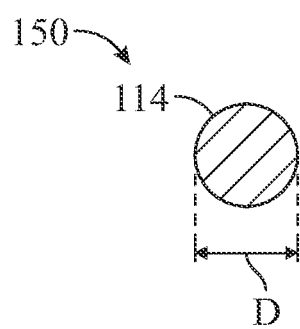
FIG. 1B is a cutaway view illustrating a portion of the device of FIG. 1A, according to an embodiment.
Figure 1C:
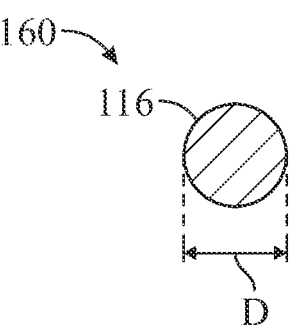
FIG. 1C is a cutaway view illustrating a portion of the device of FIG. 1A, according to an embodiment.
Figure 1D:
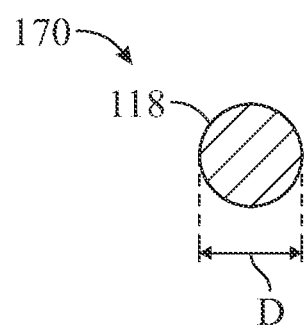
FIG. 1D is a cutaway view illustrating a portion of the device of FIG. 1A, according to an embodiment.

FIG. 1B is a cross-sectional view of first end portion 114. The cross-sectional view illustrates first end portion 114 has a substantially circular shape 150. FIG. 1C is a cross-sectional view of middle portion 116. The cross-sectional view illustrates middle portion 116 having a substantially circular shape 160. FIG. 1D is a cross-sectional view of second end portion 118. The cross-sectional view illustrates second end portion 118 has a substantially circular shape 170. First end portion 114, middle portion 116, and second end portion 118 can independently have a diameter (D) of about 4 mm to about 8 mm, such as about 5 mm to about 7 mm, such as about 5.5 mm to about 6.5 mm, such as about 6 mm. Alternatively, first end portion 114, middle portion 116, and second end portion 118 can independently have a diameter (D) of about 1 mm to about 5 mm, such as about 1.5 mm to about 3.5 mm, such as about 2 mm to about 3 mm, such as about 2.5 mm. In some embodiments, the diameter of each of the first end portion 314, middle portion 316, and second end portion 318 is substantially the same.

Taken together, a substantially circular shape of first end portion 114, middle portion 116, and second end portion 118 provides a device 100 having a substantially tubular (e.g., curvilinear tubular, e.g., curvilinear filled/solid tubular) shape. For example, device 100 has 90% or greater of portions having a substantially circular diameter of about 4 mm to about 8 mm, such as about 5 mm to about 7 mm, such as about 5.5 mm to about 6.5 mm, such as about 6 mm.

Device 100 may be substantially straight (e.g., from a top view of device 100 relative to (e.g., parallel with) horizontal axis 108 (x-axis)) and be allowed to curve rearward upon insertion into a user's buccal cavity between the upper gums and upper lip. Alternatively, device 100 may be molded to have a rearward curvature (e.g., from a top view of device 100 relative to (e.g., is not parallel to) horizontal axis 108 (x-axis)) such that device 100 even when not being used curves rearward to conform with a user's buccal cavity when in use.

Figure 2A:
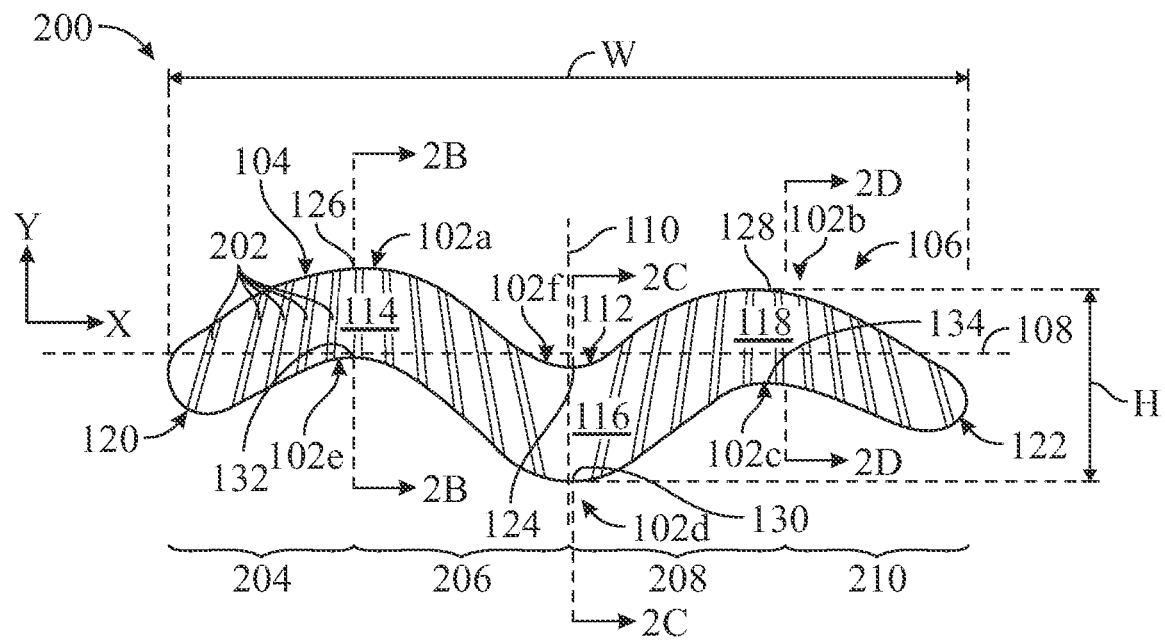
FIG. 2A is a front view illustrating a device for ceasing epistaxis, according to an embodiment.
Figures 2B, 2C, 2D:
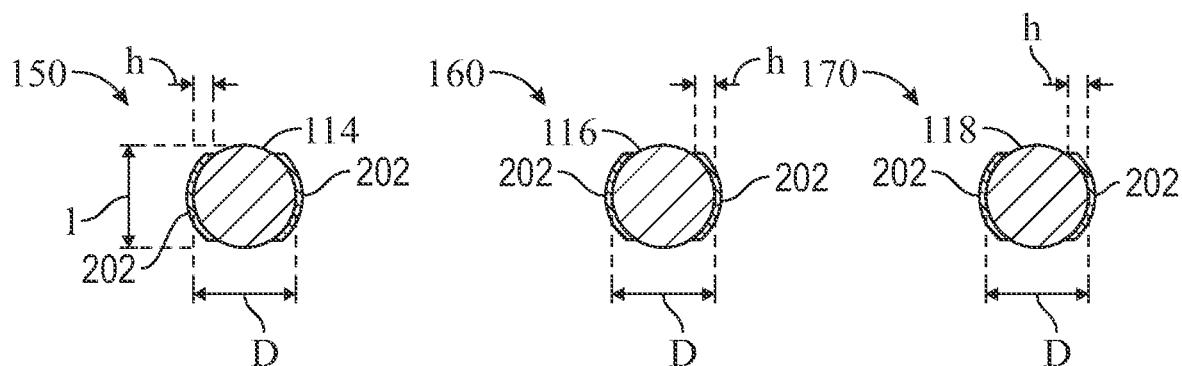
FIG. 2B is a cutaway view illustrating a portion of the device of FIG. 2A, according to an embodiment.
FIG. 2C is a cutaway view illustrating a portion of the device of FIG. 2A, according to an embodiment.
FIG. 2D is a cutaway view illustrating a portion of the device of FIG. 2A, according to an embodiment.

In some embodiments which can be combined with other embodiments, the curvilinear sidewalls and/or end caps have a plurality of protrusions. As shown in FIG. 2A, device 200 of FIG. 2A has the same design as device 100 of FIG. 1A except device 200 of FIG. 2A further includes a plurality of protrusions 202. The protrusions 202 can have a substantially vertical orientation (e.g., perpendicular to a surface of the device 200 and/or the horizontal axis 108 of the device 200. Nonetheless, one or more of the protrusions 202 can be disposed at an angle relative to vertical axis 110, such as an angle of about 1° to about 45°, such as about 1° to about 30°, such as about 1° to about 10°, such as about 3° to about 5°, alternatively about −1° to about −45°, such as about −1° to about −30°, such as about −1° to about −10°, such as about −3° to about −5°. A protrusion 202 that extends from peak point 126 toward valley point 132 is substantially parallel with vertical axis 110, and a protrusion 202 that extends from peak 128 toward valley point 134 is substantially parallel with vertical axis 110. Protrusions 202 can have a height "h" (a vertical distance extending from a peak to a valley of the protrusion). For example, protrusions can have an average height of about 2 mm to about 4 mm. Protrusions can circumscribe the device 200 or, as shown in FIGS. 2A-2D, can have a first end and second end and can have a length "l" (along the surface of the device) of about 6 mm to about 10 mm. In some embodiments, length "l" is slightly less than the average diameter "D" of device 200. In some embodiments which can be combined with other embodiments, a plurality of protrusions of a device of the present disclosure can include one protrusion to about 50 protrusions, such as about 2 protrusions to about 25 protrusions, such as about 10 protrusions to about 20 protrusions. However, more or less protrusions is also contemplated.

In some embodiments, the relative angulation of portions of protrusions 202 of device 200 can be utilized to promote a grip of the protrusions to a user's lip and/or gums during use. For example, a first portion 204 of device 200 can be such that protrusions 202 are angulated from peak point 126 toward end cap 120. Meanwhile, a second portion 206 can be such that protrusions 202 are angulated from peak point 126 toward peak point 130. In addition, a third portion 208 can be such that protrusions 202 are angulated from peak point 128 toward peak point 130. A fourth portion 210 can be such that protrusions 202 are angulated from peak point 128 toward end cap 122. It has been discovered that angulation of protrusions as shown in device 200 can promote a grip of the protrusions to a user's lip and/or gums during use.

Figure 3A:
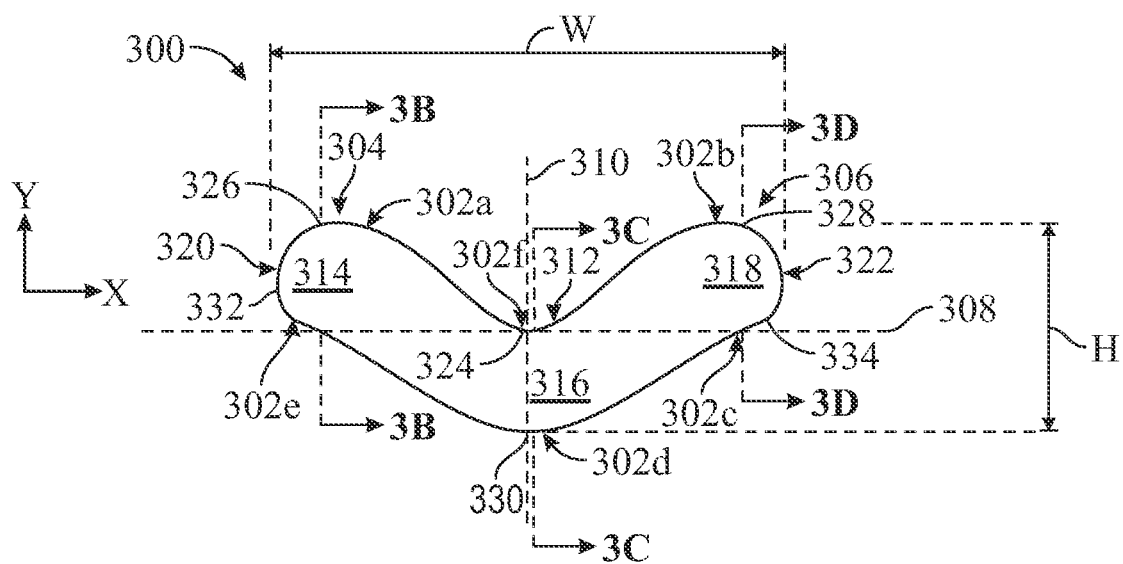
FIG. 3A is a front view illustrating a device for ceasing epistaxis, according to an embodiment.

FIG. 3A is a front view of a device 300. Device 300 is a curve-shaped material having sidewalls 302a, 302b, 302c, 302d, 302e, and 302f. Sidewalls 302a and 302b can apply pressure during use to the user's superior labial artery, the Kiesselbach plexus, and/or the greater palatine artery. While the device 200 is described as having multiple sidewalls, it is to be understood that the device 200 is a curvilinear shape that can have sidewalls continuous with one another. The terminology used herein is employed to facilitate explanation of the views shown.

Sidewalls 302d and 302f are curvilinear sidewalls. The sidewalls 302d and 302f are not horizontally extending. The device 300 has a first end 304 and second end 306 where the first end 304 and the second end 306 are disposed at an upward angle relative to a horizontal axis 308. For example, the first end 304 can extend from a middle point of device 300 (e.g., valley point 324) in an upward direction (at an angle) to sidewall 302a (e.g., peak point 326), and the upward direction is not parallel with the horizontal axis 308 and is not orthogonal to the vertical axis 310. The second end 308 can extend can extend from a middle point of device 300 (e.g., valley point 324) in an upward direction (at an angle) to sidewall 302b (e.g., peak point 328), and the upward direction is not parallel with the horizontal axis 308 and is not orthogonal to the vertical axis 310.

Device 300 has a front first end portion 314, a front second end portion 318, and a front middle portion 316. The front middle portion 316 has a curvilinear shape corresponding to curvilinear sidewall 302d and curvilinear sidewall 302f. A rear middle portion (not shown) is disposed on a side opposite of front middle portion 316, and the rear middle portion has a curvilinear shape corresponding to curvilinear sidewall 302a and curvilinear sidewall 302e.

Device 300 has a gap portion 312 shaped to fit around (e.g., nest with) a user's frenulum such that the device does not interfere with the frenulum and the device provides amelioration of epistaxis. Gap portion 312 has a valley point 324 (of sidewall 302f) provided by the descent of sidewall 302a from apex point 326 toward horizontal axis 308 and provided by the descent of sidewall 302b from apex point 328 toward horizontal axis 308.

Sidewall 302e has an end point 332 disposed opposite the apex point 326 of sidewall 302a. Sidewall 302d has an apex point 330 disposed opposite valley point 324 of sidewall 302f. Sidewall 302c has an end point 334 disposed opposite apex point 328 of sidewall 302b. In some embodiments, valley point 124 is aligned with end point 332 and end point 334 along horizontal axis 308.

Device 300 has a first end cap 320 and a second end cap 322. First end cap 320 is coupled with the front first end portion 314 at apex point 326 and end point 332 (and is coupled with the rear first end portion (not shown)). Second end cap 322 is coupled with the front second end portion 318 at apex point 328 and end point 334 (and is coupled with the rear second end portion (not shown)). In some embodiments which can be combined with other embodiments, a first end cap 320 and a second end cap 322 of a device of the present disclosure are independently selected from dome-shaped (as shown in FIG. 3A), pointed (e.g., conical ending in a point), or tapered. However, other shapes are also contemplated.

In some embodiments which can be combined with other embodiments, device 300 has a width (W) (e.g., a linear distance from first end cap 320 to second end cap 322) of about 50 millimeters (mm) to about 70 mm, such as about 55 mm to about 65 mm, such as about 57 mm to about 60 mm, such as about 58 mm. In some embodiments which can be combined with other embodiments, device 300 has a height (H) (e.g., vertical distance from peak points 326 and 328 to peak point 330) of about 10 mm to about 18 mm, such as about 12 mm to about 16 mm, such as about 13 mm to about 15 mm, such as about 14 mm.

Alternatively, device 300 has a width (W) (e.g., linear distance from first end cap 320 to second end cap 322) of about 25 millimeters (mm) to about 50 mm, such as about 28 mm to about 40 mm, such as about 29 mm to about 31 mm, alternatively about 36 mm to about 38 mm. In some embodiments, device 300 has a height (H) (e.g., vertical distance from peak points 326 and 328 to peak point 330) of about 4 mm to about 15 mm, such as about 4 mm to about 7 mm, alternatively about 9 mm to about 11 mm, such as about 10 mm.

Figure 3B:
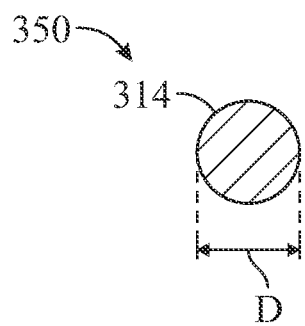
FIG. 3B is a cutaway view illustrating a portion of the device of FIG. 3A, according to an embodiment.
Figure 3C:
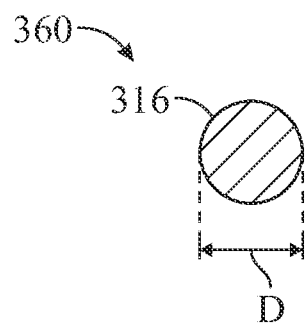
FIG. 3C is a cutaway view illustrating a portion of the device of FIG. 3A, according to an embodiment.
Figure 3D:
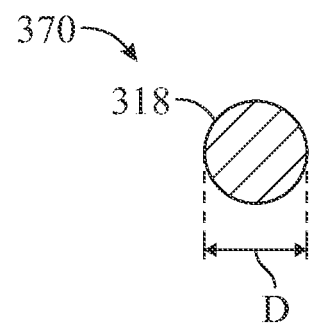
FIG. 3D is a cutaway view illustrating a portion of the device of FIG. 3A, according to an embodiment.

FIG. 3B is a cross-sectional view of first end portion 314. The cross-sectional view illustrates first end portion 314 has a substantially circular shape 350. FIG. 3C is a cross-sectional view of middle portion 316. The cross-sectional view illustrates middle portion 316 has a substantially circular shape 360. FIG. 3D is a cross-sectional view of second end portion 318. The cross-sectional view illustrates second end portion 318 has a substantially circular shape 370. First end portion 314, middle portion 316, and second end portion 318 can independently have a diameter (D) of about 4 mm to about 8 mm, such as about 5 mm to about 7 mm, such as about 5.5 mm to about 6.5 mm, such as about 6 mm. Alternatively, first end portion 314, middle portion 316, and second end portion 318 can independently have a diameter (D) of about 1 mm to about 5 mm, such as about 1.5 mm to about 3.5 mm, such as about 2 mm to about 3 mm, such as about 2.5 mm. In some embodiments, the diameter of each of the first end portion 314, middle portion 316, and second end portion 318 is substantially the same.

Taken together, a substantially circular shape of first end portion 314, middle portion 316, and second end portion 318 provides a device 300 having a substantially tubular (e.g., curvilinear tubular, e.g., curvilinear filled/solid tubular) shape. For example, device 300 has 90% or greater of portions having a substantially circular diameter of about 4 mm to about 8 mm, such as about 5 mm to about 7 mm, such as about 5.5 mm to about 6.5 mm, such as about 6 mm.

Device 300 may be substantially straight (e.g., from a top view of device 300 relative to (e.g., parallel with) horizontal axis 308 (x-axis)) and be allowed to curve rearward upon insertion into a user's buccal cavity between the upper gums and upper lip. Alternatively, device 300 may be molded to have a rearward curvature (e.g., from a top view of device 300 relative to (e.g., is not parallel with) horizontal axis 308 (x-axis)).

Figure 4A:
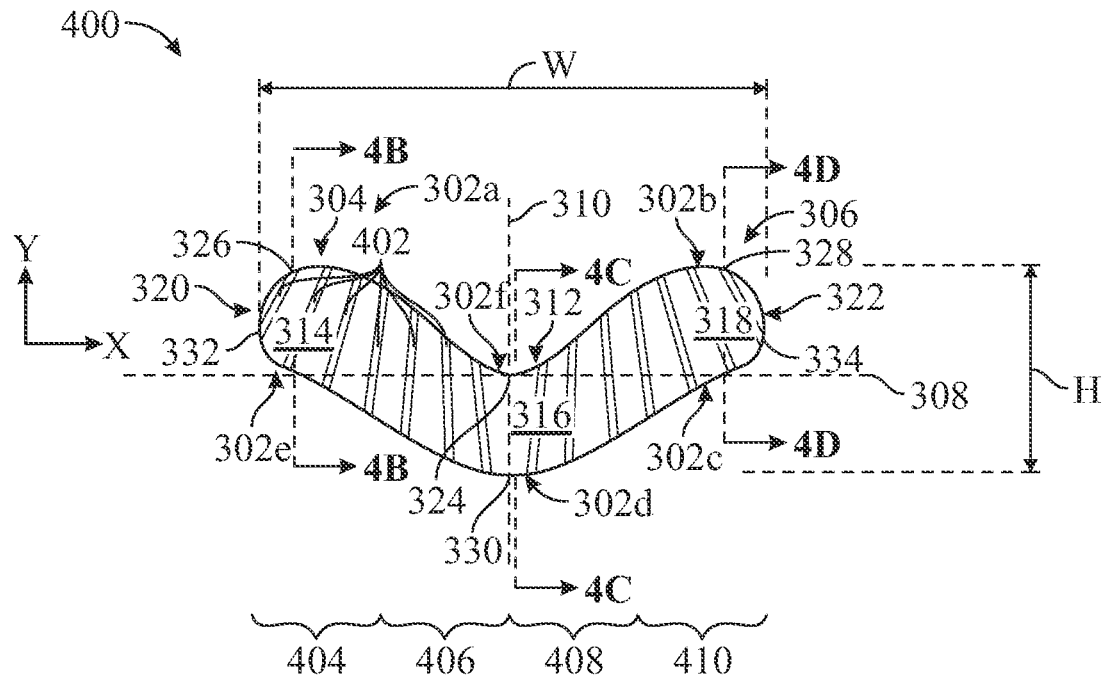
FIG. 4A is a front view illustrating a device for ceasing epistaxis, according to an embodiment.
Figure 4B:
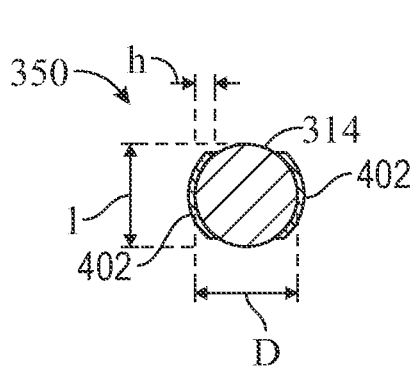
FIG. 4B is a cutaway view illustrating a portion of the device of FIG. 4A, according to an embodiment.
Figure 4C:
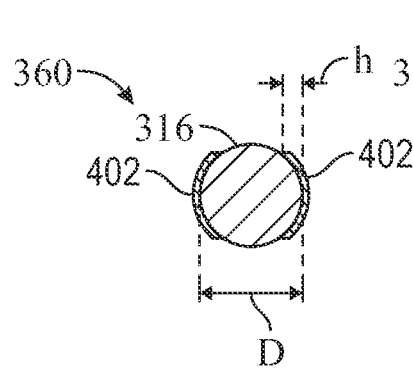
FIG. 4C is a cutaway view illustrating a portion of the device of FIG. 4A, according to an embodiment.
Figure 4D:
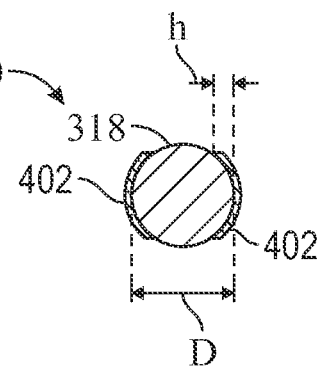
FIG. 4D is a cutaway view illustrating a portion of the device of FIG. 4A, according to an embodiment.

In some embodiments which can be combined with other embodiments, the curvilinear sidewalls and/or end caps have a plurality of protrusions. As shown in FIG. 4A, device 400 of FIG. 4A has the same design as device 300 of FIG. 3A except device 300 of FIG. 3A further includes a plurality of protrusions 402. The protrusions 402 can have a substantially vertical orientation. Nonetheless, one or more of the protrusions 402 can be disposed at an angle relative to vertical axis 310, such as an angle of about 1° to about 45°, such as about 1° to about 30°, such as about 1° to about 10°, such as about 3° to about 5°, alternatively about −1° to about −45°, such as about −1° to about −30°, such as about −1° to about −10°, such as about −3° to about −5°. Protrusions 402 can have a height "h" (a vertical distance extending from a peak to a valley of the protrusion). For example, protrusions can have an average height of about 2 mm to about 5 mm. Protrusions can circumscribe the device 400 or, as shown in FIGS. 4A-4D, protrusions can have a first end and second end and can have a length "l" of about 2 mm to about 5 mm. In some embodiments, length "l" is slightly less than the average diameter "D" of device 400. In some embodiments, a plurality of protrusions of a device of the present disclosure can include one protrusion to about 50 protrusions, such as about 2 protrusions to about 25 protrusions, such as about 10 protrusions to about 20 protrusions. However, fewer or more protrusions is also contemplated.

In some embodiments, the relative angulation of portions of protrusions 402 of device 400 can be utilized to promote a grip of the protrusions to a user's lip and/or gums during use. For example, a first portion 404 of device 400 can be such that protrusions 402 are angulated from peak point 326 toward end cap 320. Meanwhile, a second portion 406 can be such that protrusions 402 are angulated from peak point 326 toward peak point 330. In addition, a third portion 408 can be such that protrusions 402 are angulated from peak point 328 toward peak point 330. A fourth portion 410 can be such that protrusions 402 are angulated from peak point 328 toward end cap 322. It has been discovered that angulation of protrusions as shown in device 400 can promote a grip of the protrusions to a user's lip and/or gums during use.

In some embodiments, devices of the present disclosure have one or more apertures such that air can flow through the one or more apertures. A device can have one or more apertures alternatively or in addition to a plurality of protrusions.

Figure 5A:
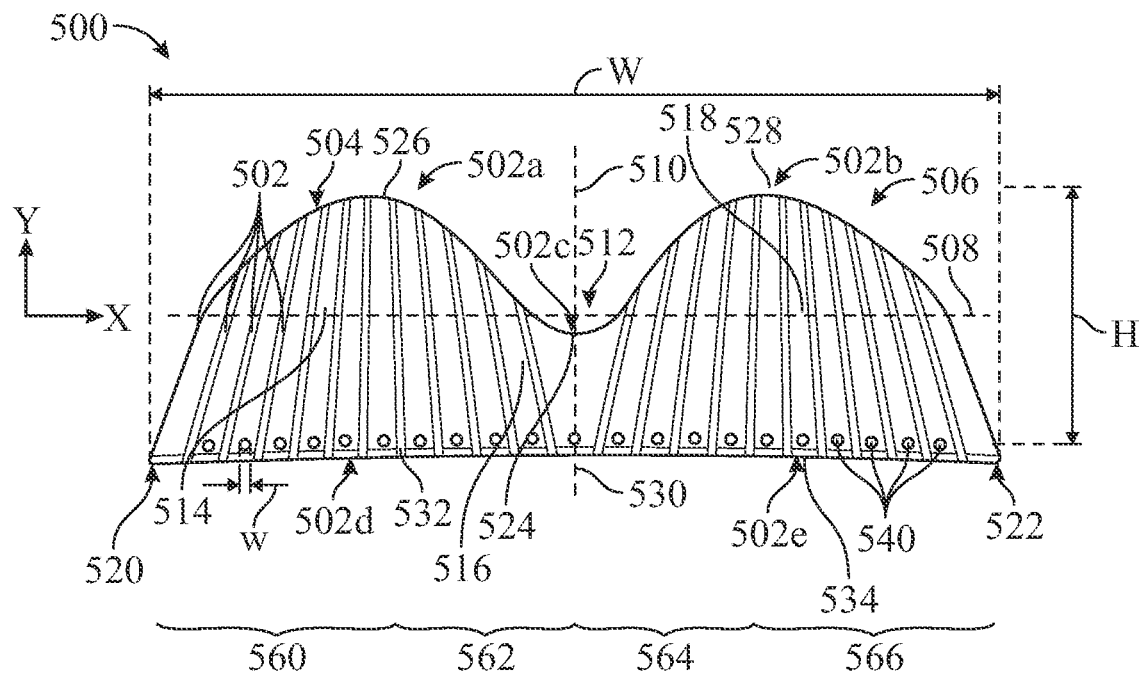
FIG. 5A is a front view illustrating a device for ceasing epistaxis, according to an embodiment.

FIG. 5A is a front view of a device 500. Device 500 has curvilinear sidewalls 502a, 502b, 502c, 502d, and 502e. As shown in FIG. 5A, sidewalls 502d and 502e have less curvature than sidewalls 502a, 502b, and 502c. In some embodiments, sidewalls 502d and 502e are substantially straight. Curvilinear sidewalls 502a and 502b can apply pressure during use to the user's superior labial artery, the Kiesselbach plexus, and/or the greater palatine artery. While the device 500 is described as having multiple sidewalls, it is to be understood that the device 500 is a curvilinear shape that can have sidewalls continuous with one another. The terminology used herein is employed to facilitate explanation of the views shown. In some embodiments, a ratio of the length of curvilinear top side (e.g., sidewalls 502a+502b+502c extending from 520 to 522) to the length of the bottom side (e.g., sidewalls 502d+502e extending from 520 to 522) is from about 1 to about 2, such as about 1.2 to about 1.5.

The curvilinear sidewalls 502a-502f are not horizontally extending, but instead the device 500 has a first end 504 and second end 506 where the first end 504 and the second end 506 are disposed at an angle relative to a horizontal axis 508. For example, the first end 504 can extend from a first curvilinear portion (e.g., apex point 526 of sidewall 502a to valley point 524 and/or to end cap 520) in a direction that is not parallel with the horizontal axis 508 and is not orthogonal to the vertical axis 510. The second end 506 can extend from a second curvilinear portion (e.g., apex point 528 of sidewall 502b to valley point 524 and/or to end cap 522) in a direction that is not parallel with the horizontal axis 508 and is not orthogonal to the vertical axis 510.

Device 500 has a front first end portion 514, a front second end portion 518, and a front middle portion 516. The front first end portion 514 has a curvilinear shape corresponding to curvilinear sidewall 502a and curvilinear sidewall 502d. A rear first end portion (not shown) is disposed on a side opposite of front first end portion 514, and the rear first end portion has a curvilinear shape corresponding to curvilinear sidewall 502a and curvilinear sidewall 502d.

The front second end portion 518 has a curvilinear shape corresponding to curvilinear sidewall 502b and curvilinear sidewall 502e. A rear second end portion (not shown) is disposed on a side opposite of front second end portion 518, and the rear first end portion has a curvilinear shape corresponding to curvilinear sidewall 502b and curvilinear sidewall 502e.

The front middle portion 516 has a curvilinear shape corresponding to curvilinear sidewall 502c (having valley point 524) and valley point 530 at the intersection of sidewall 502d with sidewall 502e. A rear middle portion (not shown) is disposed on a side opposite of front middle portion 516, and the rear middle portion has a curvilinear shape corresponding to curvilinear sidewall 502c (having valley point 524) and valley point 530 at the intersection of sidewall 502d with sidewall 502e.

Device 500 has a gap portion 512 shaped to fit around (e.g., nest with) a user's frenulum such that the device does not interfere with the frenulum and the device provides occlusion of a hemorrhage promoting epistaxis during use. Gap portion 512 has the valley point 524 (of sidewall 502c) provided by the descent of sidewall 502a from apex point 526 toward horizontal axis 508 and provided by the descent of sidewall 502b from apex point 528 toward horizontal axis 508.

Sidewall 502d has a valley point 532 disposed opposite the apex point 526 of sidewall 502a. In addition, valley point 530 is disposed opposite valley point 524 of sidewall 502c. Sidewall 502e has a valley point 534 disposed opposite apex point 528 of sidewall 502b.

Device 500 has a first end cap 520 and a second end cap 522. In some embodiments, a first end cap 520 and a second end cap 522 of a device of the present disclosure are independently selected from dome-shaped, pointed (e.g., conical ending in a point), wing-tipped (as shown in FIG. 5A), or tapered. However, other shapes are also contemplated.

Device 500 further includes a plurality of protrusions 502. The protrusions 502 can have a substantially vertical orientation. Nonetheless, one or more of the protrusions 502 can be disposed at an angle relative to vertical axis 510, such as an angle of about 1° to about 45°, such as about 1° to about 30°, such as about 1° to about 10°, such as about 3° to about 5°, alternatively about −1° to about −45°, such as about −1° to about −30°, such as about −1° to about −10°, such as about −3° to about −5°. A protrusion 502 that extends from peak point 526 to valley point 532 is substantially parallel with vertical axis 510, and a protrusion 502 that extends from peak 528 to valley point 534 is substantially parallel with vertical axis 510. Protrusions 502 can have a height "h" (a vertical distance extending from a peak to a valley of the protrusion). For example, protrusions can have an average height of about 2 mm to about 4 mm. Protrusions can circumscribe the device 500 or, as partially shown in FIG. 5B, can have a first end and second end and can have a length "l" of about 6 mm to about 10 mm. In some embodiments, length "l" is slightly less than the height (H) of device 500. In some embodiments, a plurality of protrusions of a device of the present disclosure can include one protrusion to about 50 protrusions, such as about 2 protrusions to about 25 protrusions, such as about 10 protrusions to about 20 protrusions. However, fewer or more protrusions are also contemplated.

In some embodiments, the relative angulation of portions of protrusions 502 of device 500 can be utilized to promote a grip of the protrusions to a user's lip and/or gums during use. For example, a first portion 560 of device 500 can be such that protrusions 502 are angulated from peak point 526 toward end cap 520. Meanwhile, a second portion 562 can be such that protrusions 502 are angulated from peak point 526 toward valley point 530. In addition, a third portion 564 can be such that protrusions 502 are angulated from peak point 528 toward valley point 530. A fourth portion 566 can be such that protrusions 502 are angulated from peak point 528 toward end cap 522. It has been discovered that angulation of protrusions as shown in device 500 can promote a grip of the protrusions to a user's lip and/or gums during use.

Device 500 further includes a plurality of apertures 540. As shown in FIG. 5A, the plurality of apertures 540 is arranged in a row across a lower portion device 500. Alternatively, a plurality of apertures can be arranged in any number of geometries, such as multiple rows arranged horizontally, vertically, and/or diagonally across device 500. Apertures 540 individually have a circular shape. However, other shapes are also contemplated. In some embodiments, apertures (of a plurality of apertures) have a shape selected from circular, square, rectangular, conical, star, or combination(s) thereof. In addition, as shown in FIG. 5A, device 500 has sixteen apertures. Alternatively, a plurality of apertures of a device of the present disclosure can include one aperture to about 50 apertures, such as about 2 apertures to about 25 apertures, such as about 10 apertures to about 20 apertures. For example, an aperture traverses the entire thickness of device 500 and the aperture can have a width "w" (e.g., as seen from the view of FIG. 5A) of no wider than about 1 mm, such as about 0.1 mm to about 1 mm, such as about 0.3 mm to about 0.7 mm. However, other sizes are also contemplated.

In some embodiments which can be combined with other embodiments, device 500 has a width (W) (e.g., linear distance from first end cap 520 to second end cap 522) of about 50 millimeters (mm) to about 70 mm, such as about 55 mm to about 65 mm, such as about 57 mm to about 60 mm, such as about 58 mm. In some embodiments which can be combined with other embodiments, device 500 has a height (H) (e.g., vertical distance from peak points 526 and 528 to an end cap) of about 10 mm to about 18 mm, such as about 12 mm to about 16 mm, such as about 13 mm to about 15 mm, such as about 14 mm.

Alternatively, device 500 has a width (W) (e.g., linear distance from first end cap 520 to second end cap 522) of about 25 millimeters (mm) to about 50 mm, such as about 28 mm to about 40 mm, such as about 29 mm to about 31 mm, alternatively about 36 mm to about 38 mm. In some embodiments, device 500 has a height (H) (e.g., vertical distance from peak points 526 and 528 to an end cap) of about 4 mm to about 15 mm, such as about 4 mm to about 7 mm, alternatively about 9 mm to about 11 mm, such as about 10 mm.

Figure 5B:
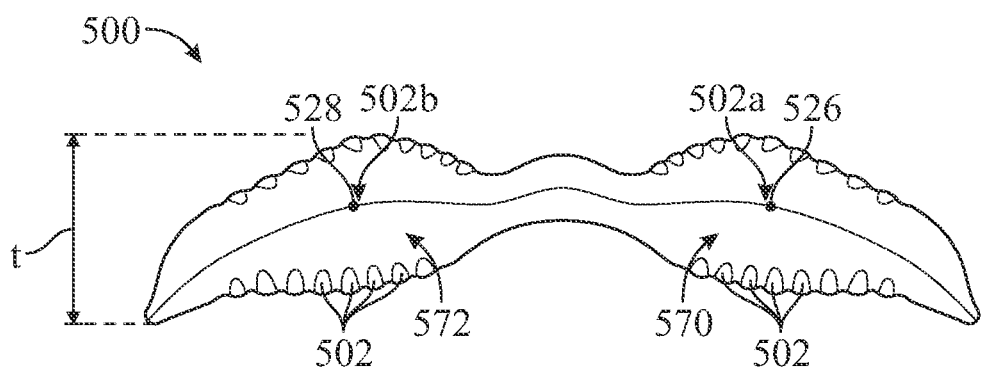
FIG. 5B is a plan view of the device of FIG. 5A, according to an embodiment.
Figure 5C:
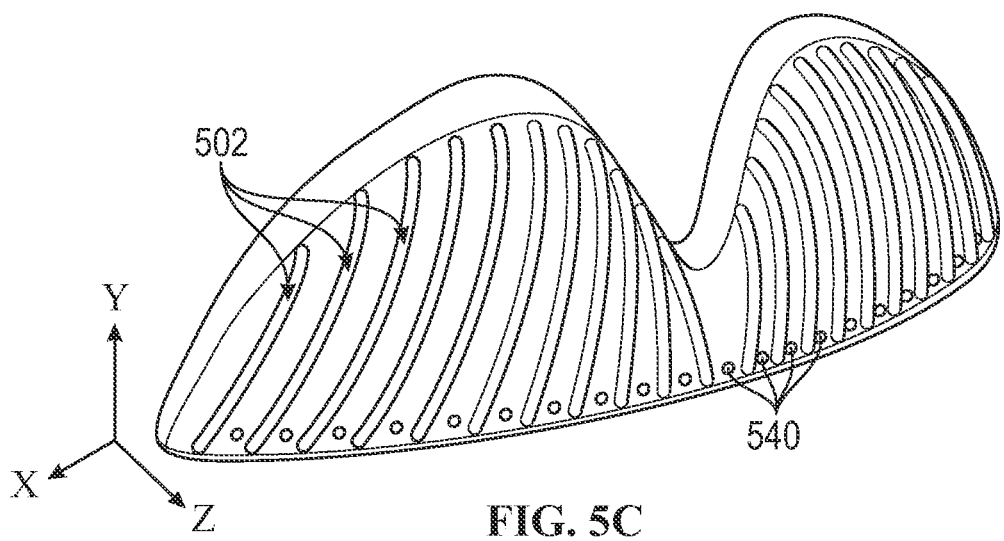
FIG. 5C is a perspective view of the device of FIG. 5A and FIG. 5B, according to an embodiment.

FIG. 5B is a plan view of device 500 of FIG. 5A. As shown in FIG. 5B, device 500 has a curvature (as viewed from the plan view), which advantageously allows device 500 to conform to a user's gums during use. Device 500 has a first lobe 570 and a second lobe 572. During use of device 500, first lobe 570 and second lobe 572 can apply pressure to the user's superior labial artery, the Kiesselbach plexus, and/or the greater palatine artery. First lobe 570 and second lobe 572 can independently have a thickness "t" of about 2 mm to about 4 mm, alternatively about 1 mm to about 3 mm. In addition, a lower portion of device 500 (e.g., the lower portion of device 500 having the plurality of apertures 540 shown in FIG. 5A) disposed below first lobe 570 and second lobe 572 can have a thickness that is less than the thickness "t" of first lobe 570 and/or second lobe 572. For example, a lower portion of device 500 can have an average thickness of about 1 mm to about 3 mm, alternatively about 0.5 mm to about 2 mm. The thickness of the lower portion of device 500 can be the same as the distance an aperture traverses through device 500. Accordingly, in some embodiments, it can be advantageous to provide apertures for a device of the present disclosure in locations of the device that are not as thick as the lobes (e.g., lobes 570 and/or 572), improving air flow through the device in the event the device might be swallowed during use. In addition, a thickness "t" of the lobes (e.g., lobes 570 and/or 572) that is greater than a thickness of a lower portion of the device (e.g., device 500) provides an opportunity for a user's lip to partially circumscribe device 500 during use allowing the lip to squeeze the device, further improving the grip on the device between the gums and lip of the user.

Figure 6:
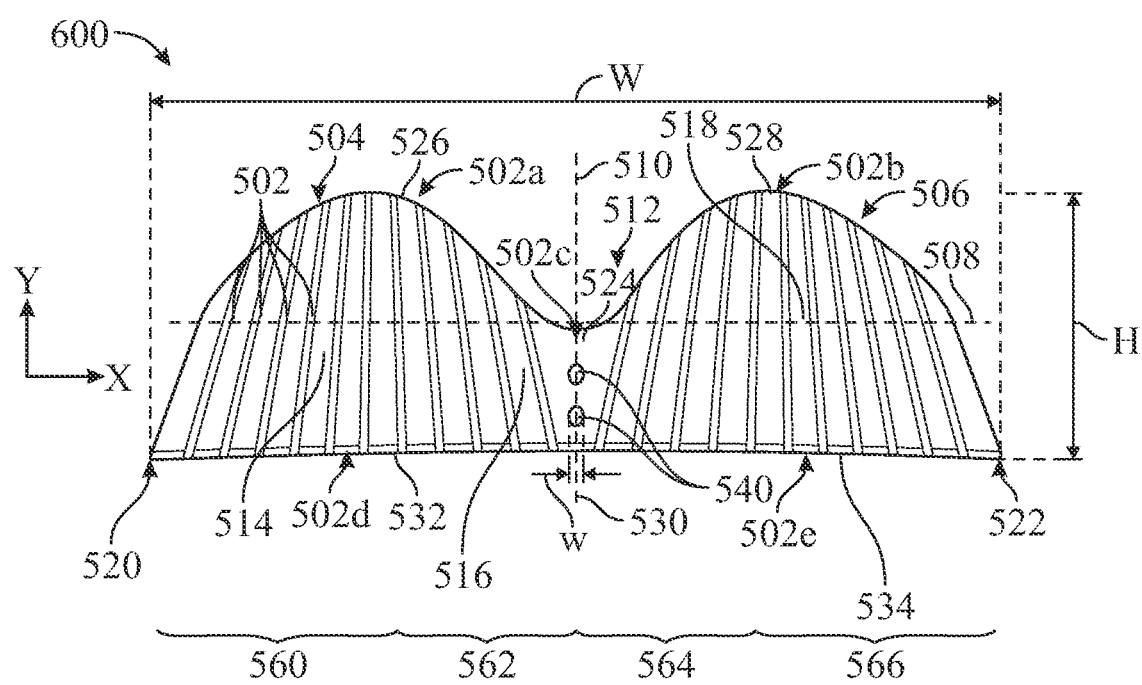
FIG. 6 is a front view illustrating a device for ceasing epistaxis, according to an embodiment.

FIG. 6 is a front view of a device 600. Device 600 is substantially the same as device 500 of FIGS. 5A-5B except the plurality of apertures 540 of device 600 is oriented vertically in a row. In addition, device 600 has two apertures 540 (instead of the sixteen apertures 540 of device 500).

Figure 7A:
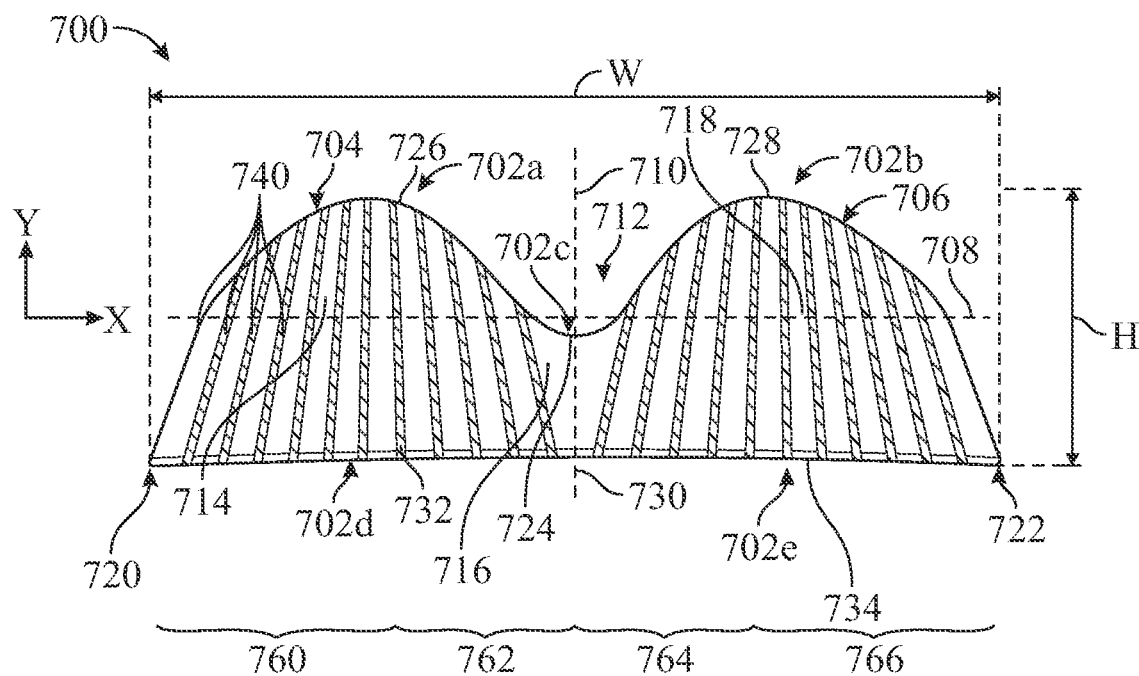
FIG. 7A is a front view illustrating a device for ceasing epistaxis, according to an embodiment.

In some embodiments which can be combined with other embodiments, devices of the present disclosure have one or more apertures such that air can flow through the one or more apertures, and the apertures are substantially vertical (e.g., commensurate with the y-axis) and elongated. FIG. 7A is a front view of a device 700. Device 700 has curvilinear sidewalls 702a, 702b, 702c, 702d, and 702e. As shown in FIG. 7A, sidewalls 702d and 702e have less curvature than sidewalls 702a, 702b, and 702c. In some embodiments, sidewalls 702d and 702e are substantially straight. Curvilinear sidewalls 702a and 702b can apply pressure during use to the user's superior labial artery, the Kiesselbach plexus, and/or the greater palatine artery. While the device 700 is described as having multiple sidewalls, it is to be understood that the device 700 is a curvilinear shape that can have sidewalls continuous with one another. The terminology used herein is employed to facilitate explanation of the views shown. In some embodiments, a ratio of the length of curvilinear top side (e.g., sidewalls 702a+702b+702c extending from 720 to 722) to the length of the bottom side (e.g., sidewalls 702d+702e extending from 720 to 722) is from about 1 to about 2, such as 1.2 to about 1.5.

The curvilinear sidewalls 702a-702f are not horizontally extending, but instead the device 700 has a first end 704 and second end 706 where the first end 704 and the second end 706 are disposed at an angle relative to a horizontal axis 708. For example, the first end 704 can extend from a first curvilinear portion (e.g., apex point 726 of sidewall 702a to valley point 724 and/or to end cap 720) in a direction that is not parallel with the horizontal axis 708 and is not orthogonal to the vertical axis 710. The second end 706 can extend from a second curvilinear portion (e.g., apex point 728 of sidewall 702b to valley point 724 and/or to end cap 722) in a direction that is not parallel with the horizontal axis 708 and is not orthogonal to the vertical axis 710.

Device 700 has a front first end portion 714, a front second end portion 718, and a front middle portion 716. The front first end portion 714 has a curvilinear shape corresponding to curvilinear sidewall 702a and curvilinear sidewall 702d. A rear first end portion (not shown) is disposed on a side opposite of front first end portion 714, and the rear first end portion has a curvilinear shape corresponding to curvilinear sidewall 702a and curvilinear sidewall 702d.

The front second end portion 718 has a curvilinear shape corresponding to curvilinear sidewall 702b and curvilinear sidewall 702e. A rear second end portion (not shown) is disposed on a side opposite of front second end portion 718, and the rear first end portion has a curvilinear shape corresponding to curvilinear sidewall 702b and curvilinear sidewall 702e.

The front middle portion 716 has a curvilinear shape corresponding to curvilinear sidewall 702c (having valley point 724) and valley point 730 at the intersection of sidewall 702d with sidewall 702e. A rear middle portion (not shown) is disposed on a side opposite of front middle portion 716, and the rear middle portion has a curvilinear shape corresponding to curvilinear sidewall 702c (having valley point 724) and valley point 730 at the intersection of sidewall 702d with sidewall 702e.

Device 700 has a gap portion 712 shaped to fit around (e.g., nest with) a user's frenulum such that the device does not interfere with the frenulum and the device provides occlusion of a hemorrhage promoting epistaxis during use. Gap portion 712 has the valley point 724 (of sidewall 702c) provided by the descent of sidewall 702a from apex point 726 toward horizontal axis 708 and provided by the descent of sidewall 702b from apex point 728 toward horizontal axis 708.

Sidewall 702d has a valley point 732 disposed opposite the apex point 726 of sidewall 702a. In addition, valley point 730 is disposed opposite valley point 724 of sidewall 702c. Sidewall 702e has a valley point 734 disposed opposite apex point 728 of sidewall 702b.

Device 700 has a first end cap 720 and a second end cap 722. In some embodiments, a first end cap 720 and a second end cap 722 of a device of the present disclosure are independently selected from dome-shaped, pointed (e.g., conical ending in a point), wing-tipped (as shown in FIG. 7A), or tapered. However, other shapes are also contemplated.

Device 700 further includes a plurality of apertures 740. The apertures 740 can have a substantially vertical orientation and be elongated (e.g., vertically elongated as shown in FIG. 7A). Nonetheless, one or more of the apertures 740 can be disposed at an angle relative to vertical axis 710, such as an angle of about 1° to about 45°, such as about 1° to about 30°, such as about 1° to about 10°, such as about 3° to about 5°, alternatively about −1° to about −45°, such as about −1° to about −30°, such as about −1° to about −10°, such as about −3° to about −5°. An aperture 740 that extends from peak point 726 to valley point 732 is substantially parallel with vertical axis 710, and an aperture 740 that extends from peak 728 to valley point 734 is substantially parallel with vertical axis 710. An aperture has a first end toward a top portion of the device and second end toward a lower portion of the device. An aperture can have a length "l" (distance between the first end and the second end of the aperture) of about 0.1 mm to about 40 mm, such as about 5 mm to about 30 mm, such as about 5 mm to about 20 mm, such as about 5 mm to about 10 mm. In some embodiments, length "l" is slightly less than the height (H) of device 700. In some embodiments, a plurality of protrusions of a device of the present disclosure can include one protrusion to about protrusions, such as about 2 protrusions to about 25 protrusions, such as about 10 protrusions to about 20 protrusions. However, fewer or more protrusions are also contemplated.

In some embodiments, the relative angulation of portions of apertures 740 of device 700 can be utilized to provide a corresponding angulation of the remaining material and the apertures of the device (e.g., the remaining material and the apertures per se) to promote a grip of the remaining material to a user's lip and/or gums during use. For example, a first portion 760 of device 700 can be such that apertures 740 are angulated from peak point 726 toward end cap 720. Meanwhile, a second portion 762 can be such that apertures 740 are angulated from peak point 726 toward valley point 730. In addition, a third portion 764 can be such that apertures 740 are angulated from peak point 728 toward valley point 730. A fourth portion 766 can be such that apertures 740 are angulated from peak point 728 toward end cap 722. It has been discovered that angulation of apertures 740 as shown in device 700 can promote a grip of the remaining material and apertures to a user's lip and/or gums during use.

As shown in FIG. 7A, device 700 has twenty three apertures. Alternatively, a plurality of apertures of a device of the present disclosure can include one aperture to about 50 apertures, such as about 2 apertures to about 25 apertures, such as about 10 apertures to about 20 apertures. Apertures of the present disclosure can have a size. For example, an aperture traverses the entire thickness of device 700 and the aperture can have a width "w" (e.g., as seen from the view of FIG. 7A) of no wider than about 1 mm, such as about 0.1 mm to about 1 mm, such as about 0.3 mm to about 0.7 mm.

In some embodiments, device 700 has a width (W) (e.g., linear distance from first end cap 720 to second end cap 722) of about 50 millimeters (mm) to about 70 mm, such as about 55 mm to about 65 mm, such as about 57 mm to about 60 mm, such as about 58 mm. In some embodiments, device 700 has a height (H) (e.g., vertical distance from peak points 726 and 728 to an end cap) of about 10 mm to about 18 mm, such as about 12 mm to about 16 mm, such as about 13 mm to about 15 mm, such as about 14 mm.

Alternatively, device 700 has a width (W) (e.g., linear distance from first end cap 720 to second end cap 722) of about 25 millimeters (mm) to about 50 mm, such as about 28 mm to about 40 mm, such as about 29 mm to about 31 mm, alternatively about 36 mm to about 38 mm. In some embodiments, device 700 has a height (H) (e.g., vertical distance from peak points 726 and 728 to an end cap) of about 4 mm to about 15 mm, such as about 4 mm to about 7 mm, alternatively about 9 mm to about 11 mm, such as about 10 mm.

Figure 7B:
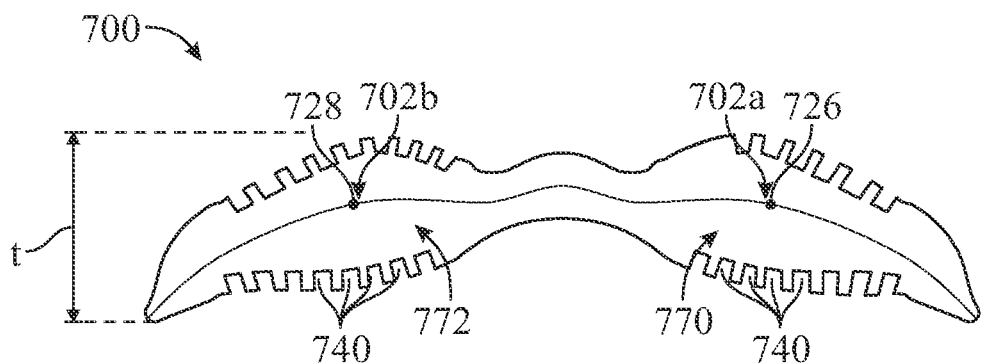
FIG. 7B is a plan view of the device of FIG. 7A, according to an embodiment.
Figure 7C:
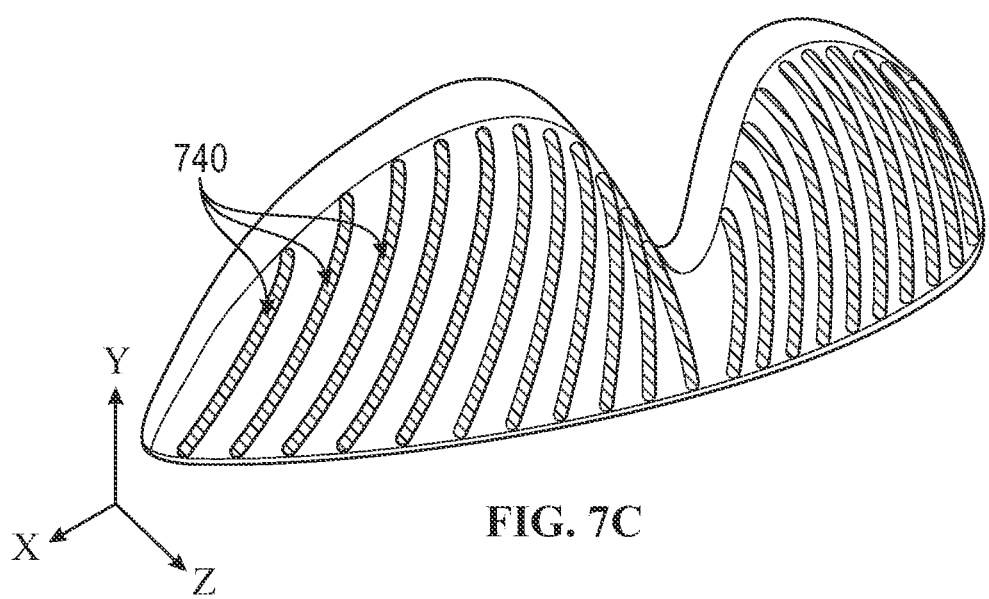
FIG. 7C is a perspective view of the device of FIG. 5A and FIG. 5B, according to an embodiment.

FIG. 7B is a plan view of device 700 of FIG. 7A. As shown in FIG. 7B, device 700 has a curvature (as viewed from the plan view), which advantageously allows device 700 to conform to a user's gums during use. Device 700 has a first lobe 770 and a second lobe 772. During use of device 700, first lobe 770 and second lobe 772 can apply pressure to the user's superior labial artery, the Kiesselbach plexus, and/or the greater palatine artery. First lobe 770 and second lobe 772 can independently have a thickness "t" of about 2 mm to about 4 mm, alternatively about 1 mm to about 3 mm.

In addition, a lower portion of device 700 disposed below first lobe 770 and second lobe 772 can have a thickness that is less than the thickness "t" of first lobe 770 and/or second lobe 772. For example, a lower portion of device 700 can have an average thickness of about 1 mm to about 4 mm. Apertures 740 traverse through both the upper/thicker portion and the lower/thinner portion of the device 700.

In addition, a thickness "t" of the lobes (e.g., lobes 770 and/or 772) that is greater than a thickness of a lower portion of the device (e.g., device 700) provides an opportunity for a user's lip to partially circumscribe device 700 during use allowing the lip to squeeze the device, further improving the grip on the device between the gums and lip of the user.

Materials

In some embodiments which may be combined with other embodiments, a device of the present disclosure is made of a silicone, a latex, a polypropylene, a polyethylene, and combination(s) thereof. However, other materials are also contemplated. A device can be non-compressible or slightly compressible, so that a device will substantially maintain its dimensions when inserted in the buccal cavity between the upper gums and the upper lip.

In some embodiments which may be combined with other embodiments, a device is made of a material that is configured to dissolve in the buccal cavity of a user. Such material may include gelatinous sugar, such as those of candies or other foodstuffs. The material can be tailored to provide the device with sufficient time to ameliorate the epistaxis while still being edible thereafter. In some embodiments, sugar granules can be disposed over a surface of a device of the present disclosure to provide additional grip to a user's lip and/or gums during use.

Other materials that may be used include oils, flavors, or medicines (such as acetaminophen, etc.)

Methods for Producing Devices

Devices of the present disclosure can be produced in various sizes, and/or with a trim-to-fit feature, to fit various users' mouths. Alternatively, a device may be custom-made to fit a user's mouth.

In some embodiments, a device of the present disclosure is made by a molding process. A device of the present disclosure can be made by molding the device to correspond with the contours of a user's buccal cavity. Such a device may be made for a user that has particular needs regarding comfort or epistaxis issues that necessitate a custom fit.

In some embodiments, a device of the present disclosure is made by a 3-dimensional printing process.

Methods for Using Devices

In some embodiments, methods of the present disclosure include introducing a device into a buccal cavity of a mouth of a user. Introducing can include introducing the device behind the user's upper lip and in front of the user's upper gums. Epistaxis can cease within seconds of introducing a device of the present disclosure to the buccal cavity at a location behind the upper lip and in front of the upper gums (such that the gap of the device is disposed around (e.g., nested with) the user's frenulum). In some embodiments, epistaxis can cease within about 30 seconds or less, such as about 10 seconds or less, such as about 5 seconds or less. In addition, use of a device of the present disclosure does not require medical training or knowledge in order to cease the epistaxis.

Overall, devices of the present disclosure having curvilinear sidewalls having a plurality of protrusions and/or apertures provides non-invasive, painless devices for treating (e.g., ceasing) epistaxis. Devices and methods of the present disclosure do not require continual positional adjustment by the user, and the devices are substantially or entirely inconspicuous to outside observers during use by the user. Devices of the present disclosure provide a simply inserted oral device which creates occlusion of the structures associated with anterior epistaxis, occluding the flow of blood to the location of the hemorrhage responsible for the epistaxis. In addition, protrusions and/or apertures of devices of the present disclosure can provide (1) the device to stay in place while occluding flow of blood to a hemorrhage and (2) substantial or complete reduction in risk of a user inadvertently swallowing the device. In the event a device might be swallowed, devices of the present disclosure may include one or more apertures such that air can flow through the one or more apertures.

In addition, devices of the present disclosure can occlude a hemorrhage to stop anterior epistaxis without nasal packing, unlike a nasal tampon, leaving the nostril free from obstruction. Insertion and removal of devices of the present disclosure is painless, providing less fear for a user. In addition, risk of opening a clot upon removal of the device is substantially less (e.g., eliminated), as compared to nasal tampons and balloon-like devices. In addition, devices of the present disclosure do not require substantial training on how to use the devices, as compared to nasal tampons and balloon-like devices. In addition, devices of the present disclosure are small (e.g., as compared to devices having a stem or a bite tab) making the devices easy to transport without taking up substantial space (e.g., the devices can be transported in a user's pocket).

Additional Aspects

The present disclosure provides, among others, the following aspects, each of which may be considered as optionally including any alternate aspects.

Clause 1. A device for occluding epistaxis, the device comprising:
- a first curvilinear wall, a second curvilinear wall, and a third curvilinear wall each disposed at a top portion of the device, the device having an x-axis, y-axis, and z-axis, wherein the top portion is relative to the y-axis;
- a fourth wall and a fifth wall each disposed at a bottom portion relative to the y-axis, the fourth wall and the fifth wall independently are substantially straight or curvilinear;
- a first end comprising a front first end portion and a back first end portion, the first end is curvilinear corresponding to the first curvilinear wall, the first end disposed at an angle relative to the x-axis;
- a second end comprising a front second end portion and a back second end portion, the second end is curvilinear and continuous with the third curvilinear wall, the second end disposed at an angle relative to the x-axis;
- a middle portion comprising a front middle portion and a back middle portion, the middle portion is curvilinear and continuous with the second curvilinear wall;
- one or more protrusions having a substantially commensurate orientation relative to the y-axis; and
- one or more apertures disposed through the device.

Clause 2. The device of Clause 1, wherein the one or more protrusion is a plurality of protrusions, and each protrusion of the plurality of protrusions is independently disposed at an angle, relative to the y-axis, of about 1° to about 10° or about −1° to about −10°.

Clause 3. The device of Clauses 1 or 2, wherein:
- a protrusion of the one or more protrusions extends from a peak point of the first curvilinear wall to a valley point of the fourth wall, and
- the protrusion of the one or more protrusions is substantially parallel with the y-axis.

Clause 4. The device of any of Clauses 1 to 3, wherein:
- a second protrusion of the one or more protrusions extends from a peak point of the third curvilinear wall to a valley point of the fifth wall, and
- the second protrusion of the one or more protrusions is substantially parallel with the y-axis.

Clause 5. The device of any of Clauses 1 to 4, wherein the one or more protrusions comprises about 10 protrusions to about 20 protrusions.

Clause 6. The device of any of Clauses 1 to 5, wherein:
- the one or more protrusions is a plurality of protrusions;
- a first portion of protrusions of the plurality of protrusions is disposed at an angle of about 1° to about 10° relative to the y-axis;
- a second portion of protrusions of the plurality of protrusions is disposed at an angle of about −1° to about −10° relative to the y-axis;
- a third portion of protrusions of the plurality of protrusions is disposed at an angle of about 1° to about 10° relative to the y-axis;
- a fourth portion of protrusions of the plurality of protrusions is disposed at an angle of about −1° to about −10° relative to the y-axis;
- the second portion is disposed between the first portion and the third portion; and
- the third portion is disposed between the second portion and the fourth portion.

Clause 7. The device of any of Clauses 1 to 6, wherein the first end has an end cap that has a wing-tipped shape and the second end has an end cap that has a wing-tipped shape.

Clause 8. The device of any of Clauses 1 to 7, wherein:
- the one or more apertures is a plurality of apertures disposed as a row across a lower portion of the device, wherein the lower portion is relative to the y-axis;
- the first curvilinear wall forms a first lobe and the second curvilinear wall forms a second lobe; and
- the first lobe and the second lobe have a thickness that is greater than a thickness of the lower portion of the device.

Clause 9. The device of any of Clauses 1 to 8, wherein the one or more apertures is a plurality of apertures, the plurality of apertures comprising about 10 apertures to about 20 apertures.

Clause 10. The device of any of Clauses 1 to 9, wherein the device has:
- a width of about 50 mm to about 70 mm; and
- a height of about 10 mm to about 18 mm.

Clause 11. The device of any of Clauses 1 to 10, wherein the one or more apertures is a plurality of apertures disposed as a row in the middle portion of the device and is disposed along the y-axis.

Clause 12. The device of any of Clauses 1 to 11, wherein the row comprises about 2 apertures to about 4 apertures.

Clause 13. A device for occluding epistaxis, the device comprising:
- a first curvilinear wall, a second curvilinear wall, and a third curvilinear wall each disposed at a top portion of the device, the device having an x-axis, y-axis, and z-axis, wherein the top portion is relative to the y-axis;
- a fourth wall and a fifth wall each disposed at a bottom portion of the device, the fourth wall and the fifth wall independently are substantially straight or curvilinear;
- a first end comprising a front first end portion and a back first end portion, the first end is curvilinear corresponding to the first curvilinear wall, the first end disposed at an angle relative to the x-axis;

a second end comprising a front second end portion and a back second end portion, the second end is curvilinear and continuous with the third curvilinear wall, the second end disposed at an angle relative to the x-axis;

a middle portion comprising a front middle portion and a back middle portion, the middle portion is curvilinear and continuous with the second curvilinear wall; and one or more apertures disposed through the device.

Clause 14. The device of Clause 13, wherein the one or more apertures is a plurality of apertures and each aperture of the plurality of apertures is independently disposed at an angle, relative to the y-axis, of about 1° to about 10° or about −1° to about −10°.

Clause 15. The device of Clauses 13 or 14, wherein:
 wherein the one or more apertures is a plurality of apertures,
 an aperture of the plurality of apertures extends from a peak point of the first curvilinear wall to a valley point of the fourth wall, and
 the aperture of the plurality of apertures is substantially parallel with the y-axis.

Clause 16. The device of any of Clauses 13 to 15, wherein:
 a second aperture of the plurality of apertures extends from a peak point of the third curvilinear wall to a valley point of the fifth wall, and
 the second aperture of the plurality of apertures is substantially parallel with the y-axis.

Clause 17. The device of any of Clauses 13 to 16, wherein the one or more apertures is a plurality of apertures and the plurality of apertures comprises about 10 apertures to about 20 apertures.

Clause 18. The device of any of Clauses 13 to 17, wherein:
 the one or more apertures is a plurality of apertures,
 a first portion of apertures of the plurality of apertures is disposed at an angle of about 1° to about 10° relative to the y-axis;
 a second portion of apertures of the plurality of apertures is disposed at an angle of about −1° to about −10° relative to the y-axis;
 a third portion of apertures of the plurality of apertures is disposed at an angle of about 1° to about 10° relative to the y-axis;
 a fourth portion of apertures of the plurality of apertures is disposed at an angle of about −1° to about −10° relative to the y-axis;
 the second portion is disposed between the first portion and the third portion; and
 the third portion is disposed between the second portion and the fourth portion.

Clause 19. The device of any of Clauses 13 to 18, wherein the device has:
 a width of about 50 mm to about 70 mm; and
 a height of about 10 mm to about 18 mm.

Clause 20. A device for occluding epistaxis, the device comprising one or more apertures.

As used herein, the terms "inner" and "outer"; "up" and "down"; "upper" and "lower"; "top" and "bottom", "vertical" and "horizontal", "upward" and "downward"; "above" and "below"; and other like terms as used herein refer to relative positions to one another and do not denote a particular direction or spatial orientation of the overall device. Such terms used herein are only used to reference a device (aspects of the device) to itself and such terms are not intended to refer to absolute orientation of the device.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As is apparent from the foregoing general description and the specific embodiments, while forms of the present disclosure have been illustrated and described, various modifications can be made without departing from the spirit and scope of the present disclosure. Accordingly, the present disclosure is not limited thereby. Likewise whenever a composition, an element or a group of elements is preceded with the transitional phrase "comprising," it is further contemplated that the same composition or group of elements with transitional phrases "consisting essentially of" "consisting of," "selected from the group of consisting of" or "is" preceding the recitation of the composition, element, or elements and vice versa may be used.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:

1. A device for occluding epistaxis, the device comprising:
 a first curvilinear wall, a second curvilinear wall, and a third curvilinear wall each disposed at a top portion of the device, the device having an x-axis, y-axis, and z-axis, wherein the top portion is relative to the y-axis;
 a fourth wall and a fifth wall each disposed at a bottom portion relative to the y-axis, the fourth wall and the fifth wall independently are substantially straight or curvilinear;
 a first end comprising a front first end portion and a back first end portion, the first end is curvilinear corresponding to the first curvilinear wall, the first end disposed at an angle relative to the x-axis;
 a second end comprising a front second end portion and a back second end portion, the second end is curvilinear and continuous with the third curvilinear wall, the second end disposed at an angle relative to the x-axis;
 a middle portion comprising a front middle portion and a back middle portion, the middle portion is curvilinear and continuous with the second curvilinear wall; and
 a plurality of protrusions each having a length having an orientation relative to the y-axis, wherein a first protrusion of the plurality of protrusions extends from a peak point of the first curvilinear wall to a valley point of the fourth wall, and the first protrusion of the plurality of protrusions has a length that is substantially parallel with the y-axis, wherein a second protrusion of the plurality of protrusions extends from the first curvilinear wall to the fourth wall, and the second protrusion of the plurality of protrusions has a length that is substantially slanted with respect to the y-axis.

2. The device of claim 1, wherein two or more protrusions of the plurality of protrusions is independently disposed at an angle, relative to the y-axis, of about 1° to about 10° or about −1° to about −10°.

3. The device of claim 1, wherein a third protrusion of the plurality of protrusions extends from a peak point of the third curvilinear wall to a valley point of the fifth wall, and the third protrusion of the plurality of protrusions is substantially parallel with the y-axis.

4. The device of claim 1, wherein a third protrusion of the plurality of protrusions extends from a peak point of the third curvilinear wall to a valley point of the fifth wall, and the third protrusion of the plurality of protrusions is substantially slanted with respect to the y-axis.

5. The device of claim 1, wherein the plurality of protrusions comprises about 10 protrusions to about 20 protrusions.

6. The device of claim 1, wherein:
protrusions of a first portion of protrusions of the plurality of protrusions are independently disposed at an angle of about 1° to about 10° relative to the y-axis;
protrusions of a second portion of protrusions of the plurality of protrusions are independently disposed at an angle of about −1° to about −10° relative to the y-axis;
protrusions of a third portion of protrusions of the plurality of protrusions are independently disposed at an angle of about 1° to about 10° relative to the y-axis;
protrusions of a fourth portion of protrusions of the plurality of protrusions are independently disposed at an angle of about −1° to about −10° relative to the y-axis;
the second portion is disposed between the first portion and the third portion; and
the third portion is disposed between the second portion and the fourth portion.

7. The device of claim 1, wherein the first end has an end cap that has a wing-tipped shape and the second end has an end cap that has a wing-tipped shape.

8. The device of claim 1, wherein the device has:
a width of about 50 mm to about 70 mm; and
a height of about 10 mm to about 18 mm.

9. The device of claim 1, wherein the fourth wall is curvilinear and the fifth wall is curvilinear.

10. The device of claim 1, wherein:
the first curvilinear wall forms a first lobe and the second curvilinear wall forms a second lobe; and
the first lobe and the second lobe have a thickness that is greater than a thickness of a lower portion of the device.

11. A method for treating epistaxis, comprising:
providing a device to a buccal cavity of a user's mouth, the device comprising:
a first curvilinear wall, a second curvilinear wall, and a third curvilinear wall each disposed at a top portion of the device, the device having an x-axis, y-axis, and z-axis, wherein the top portion is relative to the y-axis;
a fourth wall and a fifth wall each disposed at a bottom portion relative to the y-axis, the fourth wall and the fifth wall independently are substantially straight or curvilinear;
a first end comprising a front first end portion and a back first end portion, the first end is curvilinear corresponding to the first curvilinear wall, the first end disposed at an angle relative to the x-axis;
a second end comprising a front second end portion and a back second end portion, the second end is curvilinear and continuous with the third curvilinear wall, the second end disposed at an angle relative to the x-axis;
a middle portion comprising a front middle portion and a back middle portion, the middle portion is curvilinear and continuous with the second curvilinear wall; and
a plurality of protrusions each having a length having an orientation relative to the y-axis, wherein a first protrusion of the plurality of protrusions extends from a peak point of the first curvilinear wall to a valley point of the fourth wall, and the first protrusion of the plurality of protrusions has a length that is substantially parallel with the y-axis, wherein a second protrusion of the plurality of protrusions extends from the first curvilinear wall to the fourth wall, and the second protrusion of the plurality of protrusions has a length that is substantially slanted with respect to the y-axis.

12. The method of claim 11, wherein the plurality of protrusions is independently disposed at an angle, relative to the y-axis, of about 1° to about 10° or about −1° to about −10°.

13. The method of claim 11, wherein a third protrusion of the plurality of protrusions extends from a peak point of the third curvilinear wall to a valley point of the fifth wall, and the third protrusion of the plurality of protrusions is substantially parallel with the y-axis.

14. The method of claim 11, wherein the plurality of protrusions comprises about 10 protrusions to about 20 protrusions.

15. The method of claim 11, wherein:
protrusions of a first portion of protrusions of the plurality of protrusions are independently disposed at an angle of about 1° to about 10° relative to the y-axis;
protrusions of a second portion of protrusions of the plurality of protrusions are independently disposed at an angle of about −1° to about −10° relative to the y-axis;
protrusions of a third portion of protrusions of the plurality of protrusions are independently disposed at an angle of about 1° to about 10° relative to the y-axis;
protrusions of a fourth portion of protrusions of the plurality of protrusions are independently disposed at an angle of about −1° to about −10° relative to the y-axis;
the second portion is disposed between the first portion and the third portion; and
the third portion is disposed between the second portion and the fourth portion.

16. The method of claim 11, wherein the first end has an end cap that has a wing-tipped shape and the second end has an end cap that has a wing-tipped shape.

17. The method of claim 11, wherein the fourth wall is curvilinear and the fifth wall is curvilinear.

18. The method of claim 11, wherein the device has:
a width of about 50 mm to about 70 mm; and
a height of about 10 mm to about 18 mm.

19. The method of claim 11, one or more apertures disposed through the device.

20. The method of claim 19, wherein the one or more apertures is a plurality of apertures disposed as a row in the middle portion of the device and is disposed along the y-axis.

21. The method of claim 19, wherein the one or more apertures is a plurality of apertures disposed as a row across a lower portion of the device, wherein the lower portion is relative to the y-axis.

22. The method of claim 11, wherein:
the first curvilinear wall forms a first lobe and the second curvilinear wall forms a second lobe; and
the first lobe and the second lobe have a thickness that is greater than a thickness of a lower portion of the device.

23. A method for treating epistaxis, comprising:
providing a device to a buccal cavity of a user's mouth, the device comprising:
a first curvilinear wall, a second curvilinear wall, and a third curvilinear wall each disposed at a top portion of the device, the device having an x-axis, y-axis, and z-axis, wherein the top portion is relative to the y-axis;
a fourth wall and a fifth wall each disposed at a bottom portion of the device, the fourth wall and the fifth wall independently are substantially straight or curvilinear;
a first end comprising a front first end portion and a back first end portion, the first end is curvilinear corresponding to the first curvilinear wall, the first end disposed at an angle relative to the x-axis;
a second end comprising a front second end portion and a back second end portion, the second end is curvilinear and continuous with the third curvilinear wall, the second end disposed at an angle relative to the x-axis;
a middle portion comprising a front middle portion and a back middle portion, the middle portion is curvilinear and continuous with the second curvilinear wall; and
a plurality of apertures disposed through the device, wherein a first aperture of the plurality of apertures extends from a peak point of the first curvilinear wall to a valley point of the fourth wall, and the first aperture of the plurality of apertures has a length that is substantially parallel with the y-axis, wherein a second aperture of the plurality of apertures extends from the first curvilinear wall to the fourth wall, and the second aperture of the plurality of apertures has a length that is substantially slanted with respect to the y-axis.

24. The method of claim 23, wherein the plurality of apertures is independently disposed at an angle, relative to the y-axis, of about 1° to about 10° or about −1° to about −10°.

25. The method of claim 23, wherein: a third aperture of the plurality of apertures extends from a peak point of the third curvilinear wall to a valley point of the fifth wall, and the third aperture of the plurality of apertures is substantially parallel with the y-axis.

26. The method of claim 23, wherein the plurality of apertures comprises about 10 apertures to about 20 apertures.

27. The method of claim 23, wherein:
apertures of a first portion of apertures of the plurality of apertures are independently disposed at an angle of about 1° to about 10° relative to the y-axis;
apertures of a second portion of apertures of the plurality of apertures are independently disposed at an angle of about −1° to about −10° relative to the y-axis;
apertures of a third portion of apertures of the plurality of apertures are independently disposed at an angle of about 1° to about 10° relative to the y-axis;
apertures of a fourth portion of apertures of the plurality of apertures are independently disposed at an angle of about −1° to about −10° relative to the y-axis;
the second aperture is disposed between the first aperture and the third aperture; and
the third aperture is disposed between the second aperture and the fourth aperture.

28. The method of claim 23, wherein the device has:
a width of about 50 mm to about 70 mm; and
a height of about 10 mm to about 18 mm.

29. The method of claim 23, wherein the fourth wall is curvilinear and the fifth wall is curvilinear.

* * * * *